United States Patent
Kolen et al.

(10) Patent No.: US 10,152,830 B2
(45) Date of Patent: Dec. 11, 2018

(54) CAMERA-BIOMETRIC MOTION SENSOR AND METHOD OF SYNCHRONIZATION

(71) Applicants: Paul T. Kolen, Encinitas, CA (US); John Andrew Wells, Paradise Valley, AZ (US)

(72) Inventors: Paul T. Kolen, Encinitas, CA (US); John Andrew Wells, Paradise Valley, AZ (US)

(73) Assignee: JAWKU L.L.C. A DELAWARE CO., Paradise Valley, AZ (US)

( * ) Notice: Subject to any disclaimer, the term of this patent is extended or adjusted under 35 U.S.C. 154(b) by 0 days.

(21) Appl. No.: 15/932,079

(22) Filed: Jan. 31, 2018

(65) Prior Publication Data
US 2018/0225889 A1 Aug. 9, 2018

Related U.S. Application Data

(60) Provisional application No. 62/499,725, filed on Feb. 6, 2017.

(51) Int. Cl.

| | |
|---|---|
| G08B 1/00 | (2006.01) |
| G07C 1/24 | (2006.01) |
| H04W 4/02 | (2018.01) |
| A61B 5/00 | (2006.01) |

(52) U.S. Cl.
CPC .............. *G07C 1/24* (2013.01); *A61B 5/6801* (2013.01); *H04W 4/023* (2013.01)

(58) Field of Classification Search
CPC ........ G07C 1/24; G01C 22/006; G01C 22/00; A43B 3/00; G06K 9/00342; H04N 7/14; G08B 1/00; G08B 3/00

USPC ................... 340/309.16; 235/105; 348/14.14
See application file for complete search history.

(56) References Cited

U.S. PATENT DOCUMENTS

| | | | |
|---|---|---|---|
| 9,375,627 B2 * | 6/2016 | Hansen | ..................... G07C 1/24 |
| 9,704,412 B2 | 7/2017 | Wells | |
| 9,883,332 B2 * | 1/2018 | Hansen | ................... G16H 40/67 |
| 2004/0145471 A1 | 7/2004 | Lawrenson | |
| 2006/0279627 A1 * | 12/2006 | Yamamoto | ............. H04W 76/10 |
| | | | 348/14.14 |

(Continued)

OTHER PUBLICATIONS

Jimson Lee, "The Sprint Stopper Fully Automatic Timing App", http://speedendurance.com/2016/09/25/the-sprint-stopper-fully-automatic-timing-app, p. 1-4.

(Continued)

*Primary Examiner* — Toan N Pham

(57) ABSTRACT

An athlete (1) measures sprint time by locating a smartphone (3) having a camera and crystal oscillator clock which is first activated at the finish line. The sprint end time is recorded by a photo stamp time app activated by a video trigger causing the smartphone (3) to send a RF stop event signal to the athlete's wrist mounted motion sensor (2). Before this a sensor timer or clock is started via the sprinter's start event. The sprinter's start activates the sensor's clock and saves the captured start time including time drift error. Upon the phone app selecting the run time function, a sync command sent to the sensor (2) by the app zeros out the phone and sensor timers. A one-time crystal calibration routine correcting for drift errors caused by the smartphone's operating system is activated which provides the sprint with a corrected start time.

21 Claims, 4 Drawing Sheets

(56) References Cited

U.S. PATENT DOCUMENTS

| | | |
|---|---|---|
| 2007/0219744 A1 | 9/2007 | Kolen |
| 2008/0209044 A1 | 8/2008 | Forrester |
| 2010/0295943 A1* | 11/2010 | Cha .................. G01S 13/82 |
| | | 348/143 |
| 2014/0273925 A1 | 9/2014 | Burgett et al. |
| 2015/0051720 A1 | 2/2015 | James |
| 2015/0335947 A1* | 11/2015 | Kaushansky ...... A63B 24/0062 |
| | | 340/870.07 |

OTHER PUBLICATIONS

Rachel Bachman, "The Army's Radical Fitness Shift", The Wall Street Journal Life & Arts Section, Oct. 21, 2017, p. A11.
"Quick Start Quide INSTEON Motion Sensor Models: 2842-222, 2842-422, 2842-522", INSTEON, Nov. 6, 2012, XPO55318275, Retrieved from the Internet<URL:http://cache.insteon.com/documentation/2842-222-en.pdf>.
"SmartMove—Accuracy You Can Trust, Change Made Easy.", Smartmove Team., May 22, 2014, XPO55318272, Retrieved from the Internet<URL:http://www.kickstarter.com/projects/smartmove/smartmove-accuracy-you-can-trust-change-made-easy?ref+video on20160414].
Sten Kaiser.: "SprintTimer", Youtube., May 12, 2014, Retrieved from the Internet<URL:https://www.youtube.com/watch?v=nPOH91OrRsA>.

* cited by examiner

CAMERA-BIOMETRIC MOTION SENSOR AND METHOD OF SYNCHRONIZATION

CROSS-REFERENCE TO RELATED APPLICATIONS/INCORPORATED BY REFERENCE

This application makes reference to, claims priority to, and claims the benefit of U.S. Provisional Application Ser. No. 62/499,725 filed Feb. 6, 2017 entitled "Camera-Biometric Motion Sensor and Method of Synchronization". This application makes reference to and incorporates in its entirety by reference U.S. patent application Ser. No. 14/121,226 filed Aug. 14, 2014, now published as US2015-0287338A1 and entitled "BIOMETRIC DATA GATHERING" ad now U.S. Pat. No. 9,704,412B1. The present application incorporates by reference in their entirety Provisional Applications 62/178,034, filed Mar. 31, 2015, entitled "Clap-Sync Timers and Method" and 62/282,571, filed Aug. 5, 2015, and entitled "Camera-Biometric Motion Timer and Method". The present application incorporates by reference International Application No. PCT/US2016/013145 published as WO 2016/160091A1 which is a combination of the above Provisional Applications 62/178,034 and 62/282,571.

FIELD OF THE INVENTION

The present invention relates to a method by which a sole athlete can accurately time a premeasured distance traversed by the athlete using a prepositioned mobile smart device, such as a smartphone, having a camera and a photo stamp time app placed at the end of the predetermined distance to capture the run end time and a wrist mounted 6-DOF mems motion sensor such as that developed by JAWKU, L.L.C, a Delaware Company. The motion sensor captures the run start time.

BACKGROUND OF THE INVENTION AND TECHNICAL PROBLEM SOLVED

Recent smartphone security enhancements in the APPLE iOS® and the Android® operating systems result in an unacceptable uncertainty in the sensor and smartphone synchronization methods disclosed in the above referenced Provisional Applications 62/178,034 and 62/282,571 resulting in a very large, over 400 ms, potential error in the calculated run time. The present invention discloses a method whereby the actual run time is derived to reduce the residual synchronization error to +/−8 ms to thereby stay within an acceptable +/−10 ms error limit to avoid the new security induced errors. A one-time calibration routine is used to characterize the relative time drift between the crystals of the smartphone's time base and that of the motion sensor time base. Once calibrated, the relative time base drift error is fully characterized and can be used to remove the error in all future run time calculations. Once calibrated, the long term variation of the crystals, in terms of temperature and aging, is effectively negligible and can be considered constant over the life of the motion sensor.

Often an athlete in training is clocked for the time taken to cover a premeasured distance which entails a starting signal to start timing of the event and an end signal to stop timing the event. The starting signal may be an audible sound or series of sounds, such as by way of examples, a whistle, beep, siren or shot sound. For an end signal, a trainer may use a stop clock or a camera with a time stamp to determine the end of the event. It is an object of the present invention to provide a method and apparatus for training by which the athlete no longer needs a second person to clock the time taken to cover the predetermined distance thus providing maximum scheduling flexibility for the training time.

BRIEF SUMMARY OF THE INVENTION

The motion sensor worn on the wrist has a crystal oscillation timer started via the start event. To begin the start event, the athlete has the option of selecting either a track start or a self start. A stop event is generated by the photo stamp time app when the athlete passes the video trigger on the smartphone app which provides a stop time T(Stop).

Upon receiving the triggering signal, the smartphone transmits a RF (Radio Frequency) stop request to the motion sensor to cause, the sensor to capture and save the time value on receipt of the RF request. The sensor sends this captured start time T'(Start) which is really the actual start time T(Start) plus a time error T(Error) to the smartphone. The smartphone runs a previously loaded one-time crystal calibration routine to remove the time error T(Error). The difference in the start time T(Start) and the stop time T(Stop) recorded by the photo stamp time app equals the true run time. The previously mentioned security enhancements to the operating systems of the smartphones cause the unacceptable 400 ms uncertainty or delay in the motion sensor and smartphone synchronization of time bases caused by relative time base drift errors. The present invention corrects for these drift errors by having the smartphone upon receiving the start time T'(Start) run the one-time crystal calibration routine upon the smartphone receiving the captured start event time. Due to this calibration, T(error) is accurately calculated and is removed from the captured run time. This delay in synchronization can be determined at the factory manufacturing the motion sensor sparing the user from having to re-sync. As above disclosed the delay is subtracted from the measured sprint time. By performing a large number of trials at the factory, the average delay and the SD (Standard Deviation) of the delay can be characterized. The average value of the characterized delay determined at the factory is subtracted from the measured sprint time, leaving only the residual SD as the error which need be done only once at the factory.

BRIEF DESCRIPTION OF THE DRAWINGS

Further features and advantages of the present invention will be apparent upon consideration of the following detailed description of the present invention, taken in conjunction with the figures, in which like references refer to like parts, and in which.

DETAILED DESCRIPTION OF THE INVENTION

Figure 1:
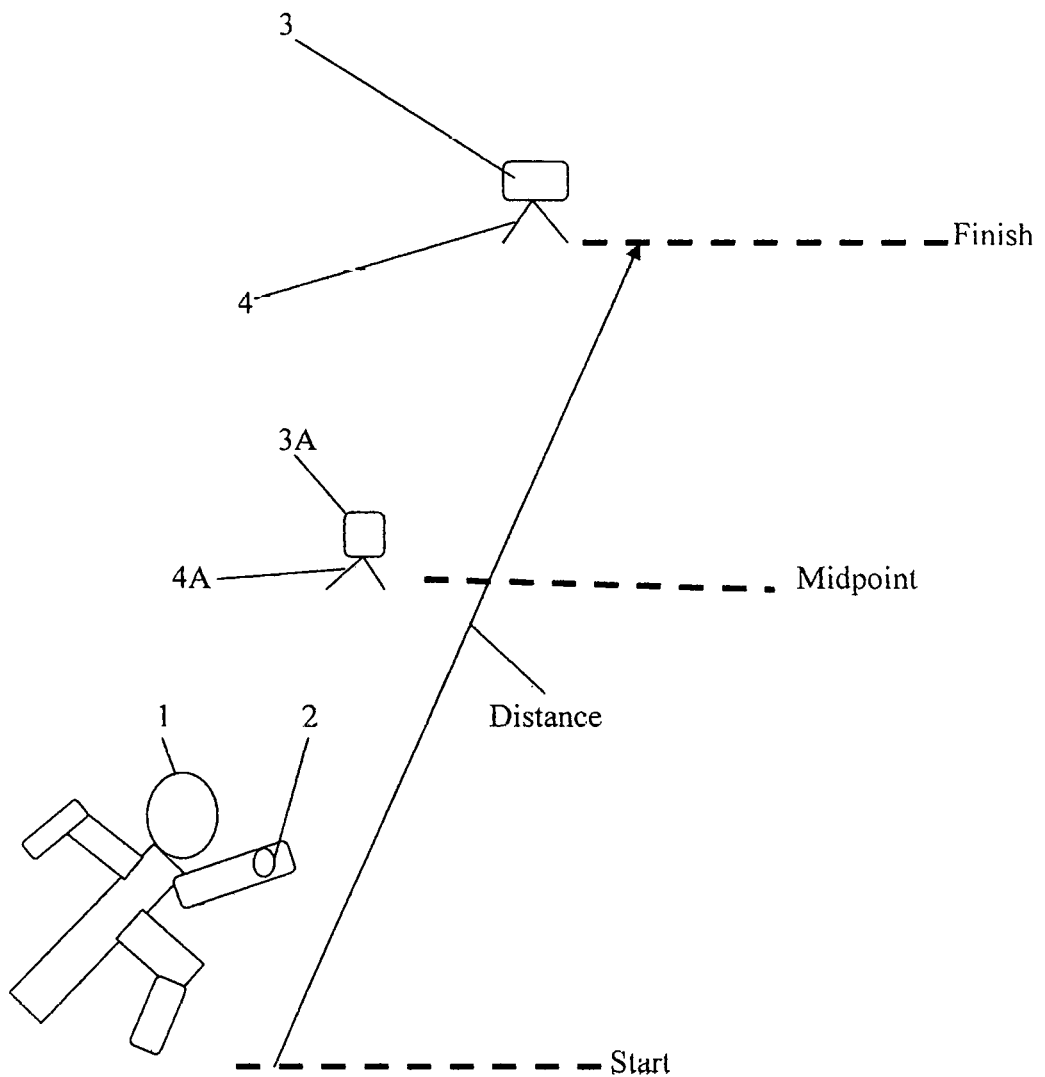
FIG. 1 schematically shows (not to scale) an athlete preparing to start to run a premeasured distance.

Referring to FIG. 1, an athlete 1, wearing a motion sensor 2 on a wrist is starting to traverse a premeasured or predetermined distance, such as a 40 yard sprint. The athlete has previously prepositioned a smart device, such as a smartphone 3, on a tripod 4. The motion sensor 2 is a 6-DOF mems more fully explained in the previously referenced U.S. patent application Ser. No. 14/121,226. In the art, the term "6-DOF" refers to six degrees of freedom represented by the x, y, and z axis of movements. The term "mems" refers to miniature electrical mechanical systems. The motion parameters are sensed using an acceleration sensor and gyroscope sensor for each axis which acceleration sensors and gyroscope sensors are integrated in the motion sensor.

Figure 2:
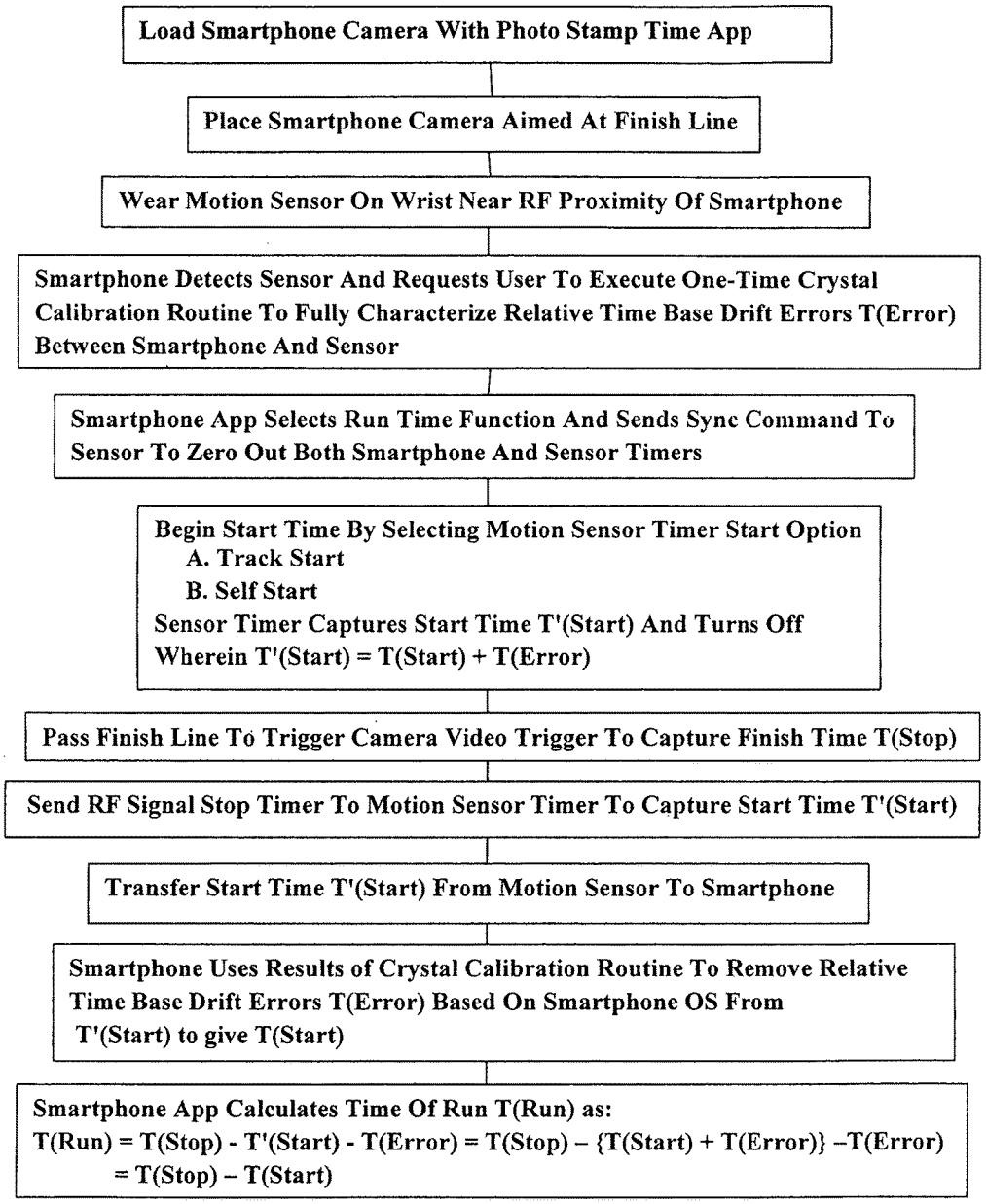
FIG. 2 depicts a flow chart of how the error compensated run time is obtained.

Referring to FIG. 2, a photo stamp time app is loaded into the smartphone to capture the finish time when the athlete crosses the finish line. The smartphone 3 has a camera which is aligned with the finish line of the predetermined distance. Passing the finish line causes a video camera trigger to capture the finish time referred to as T(Stop).

The smartphone 3 has a crystal oscillator clock. The motion sensor 2 is mounted on the athlete's wrist and has a free running clock. The smartphone detects the motion sensor when in RF proximity of the motion sensor. When the smartphone app detects the motion sensor for the first time, it tells the user a calibration is required. A one-time crystal calibration routine has been installed in the smartphone which requests the user to run the calibration routine. This calibration routine characterizes the relative time drift between the smartphone time base and the motion sensor time base and is referred to as T(Error). Once calibrated, the long-term variation of the crystals, in terms of temperature and aging, is effectively negligible and can be considered constant over the life of the sensor. Once the athlete executes the calibration the relative time base drift error is fully characterized based on the operating system of the smartphone (for example iOS® or Android®) and can be used to remove error in all future run time calculations. The smartphone app selects the run time function and sends a sync command to the sensor which command zeros out both the smartphone and sensor timers. The timing error in this single sync command is factory calibrated based on the operating system of the smartphone and is removed immediately by the sensor, so both timers are truly zeroed out. At this time, both the sensor and smartphone app timers begin to accumulate time via their respective time base.

Figure 3:
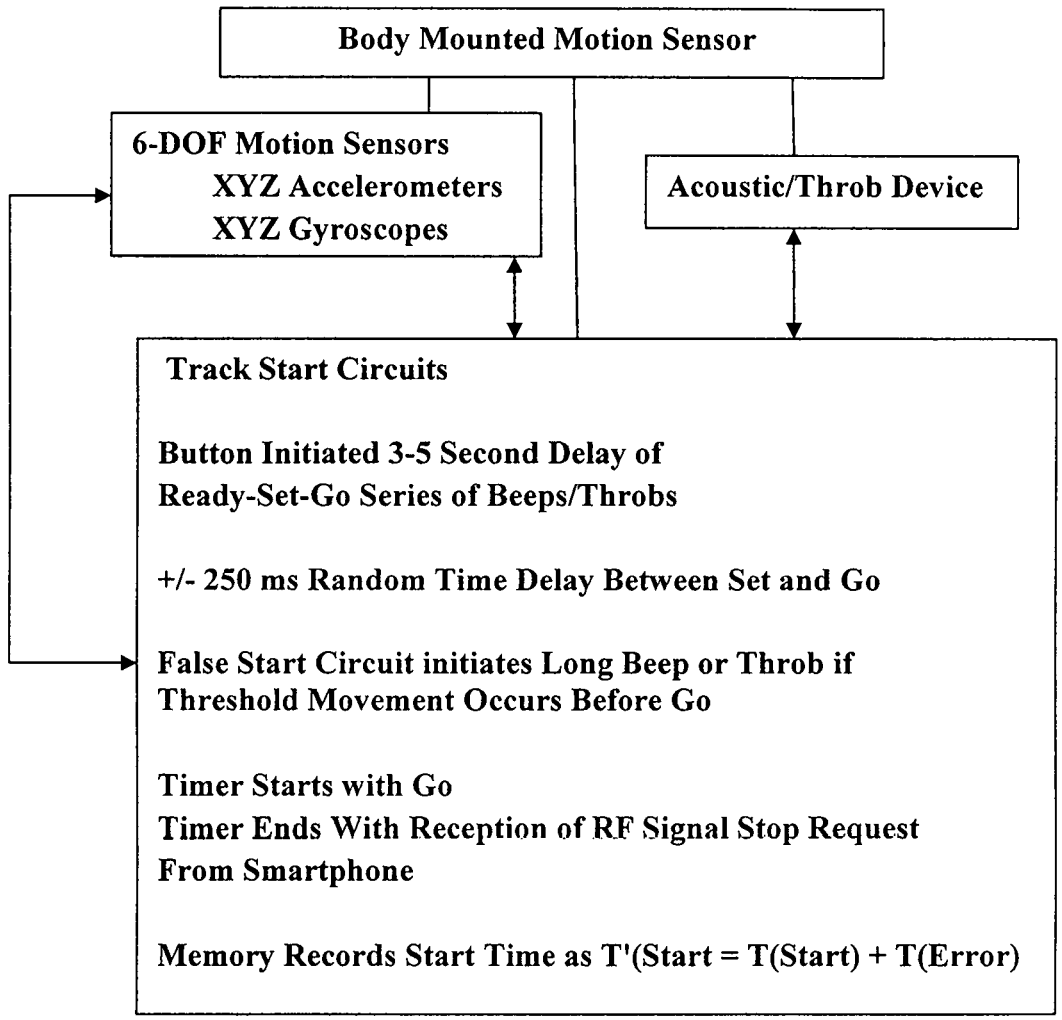
FIG. 3 is a flow chart showing the track start method.
Figure 4:
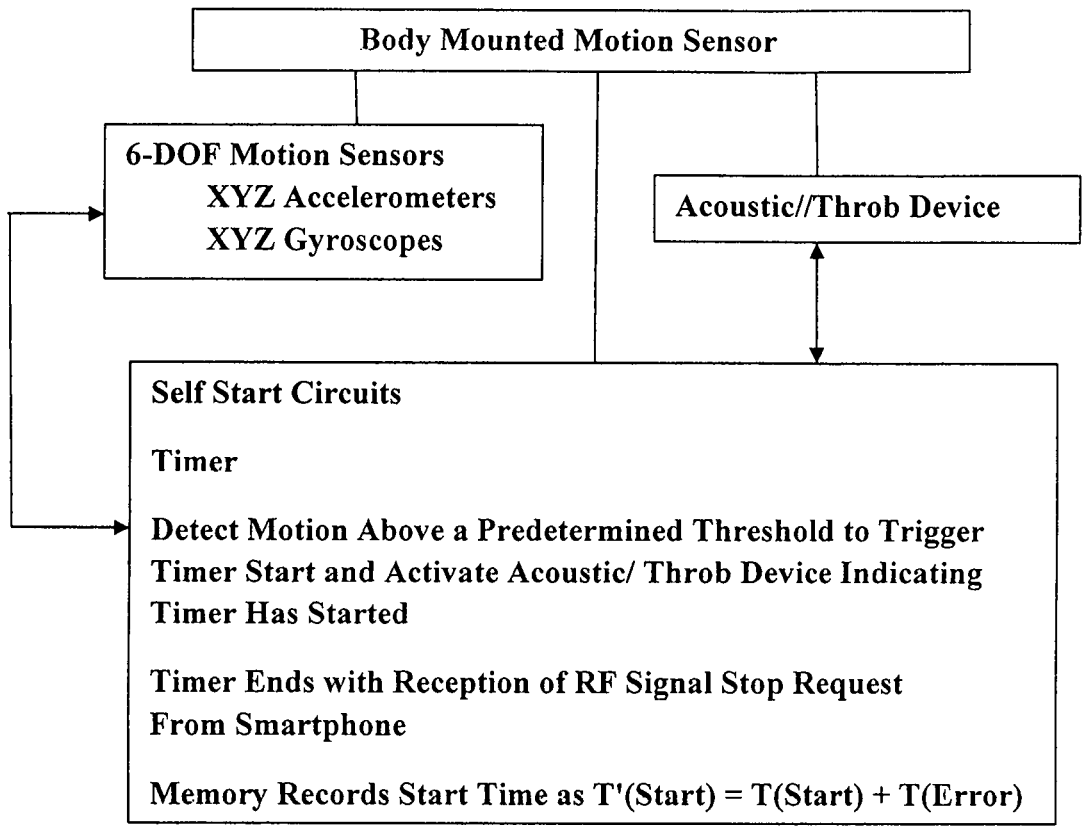
FIG. 4 is a flow chart showing the self start method.

When the athlete starts the run with either the track start disclosed in FIG. 3, or the self start disclosed in FIG. 4, the start time is captured by the sensor timer and turns off. The captured sensor start time includes the drift error and is given in FIG. 2 as:

$$T'(Start)=T(Start)+T(Error)$$

where T(Error) is the accumulated time drift error at the start time. Due to the above described calibration, T(Error) is accurately calculated and removed. All that is needed is the T'(Start), to determine T(Error).

Once the runner passes the finish line, the smartphone timer captures T(Stop) on the smartphone timer and the smartphone sends a RF command to the sensor 2 to request the sensor 2 to transfer the previously captured T'(Start) It is important to note that the amount of time between the smartphone command and the time it takes for the sensor to respond has no effect on the run time accuracy.

Once the smartphone gets the T'(Start) from the sensor, the smartphone app calculates T(Error) using T'(Start), resulting in the corrected run time being calculated as:

$$T(Run)=T(Stop)-T(Start)-T(Error)=T(Stop)-\{T(Start)+T(Error)\}-T(Error)=T(Stop)-T(Start).$$

This results in a residual error of less than +/−8 ms, well below the target of +/−10 ms.

The athlete at the starting line chooses (see FIG. 2) between two ways to detect the start of the run event and thus save the event start time. A track start app as shown in FIG. 3 or a self start app as shown in FIG. 4 is chosen which apps are preloaded into the sensor 2 using the smartphone 3. An acoustic element is incorporated into the motion sensor 2 to provide acoustic feedback to the athlete as required by the particular exercise.

In the case of choosing the track start method, the athlete goes to the starting line and prepares to start the run by pushing a start button on the motion sensor to initiate a new run event. This activates a randomly variable delayed audible start signal such as a bell, whistle, or beeping sound. For example, once the button is pushed, after a 1-5 second delay the acoustic element emits a READY-SET-GO series of beeps. The time between the SET and GO beep is randomly varied by +/−250 milliseconds (ms). This delay is made random so that the sprinter does not try to anticipate the beep count. If the runner goes before the actual GO beep, a long beep is issued to indicate a false start, requiring the runner to reset and repeat the run start. The sensor start time is saved in the internal memory of the motion sensor 2 at the instant the GO peep is emitted, thus including the runner reaction time in the overall run time. The track start method yields the user reaction time as well as the run time.

In the case of choosing the self start method, the motion sensor 2 detects the run start instead of the READY-SET-GO method. The motion sensor 2 is configured though a memory to save the start time once the sensor detects motion above a pre-determined threshold. Once the threshold is exceeded, the start time is saved and a beep is issued to indicate to the user that the start was detected. If the runner goes and DOES NOT hear the beep, the threshold was not exceeded and the run start needs to reset.

By allowing the user to select which method to be used via the smartphone app, the user can select the start method. In both cases the end time is recorded the same as above described. The RF request stop signal is sent to the timer of the motion sensor 2. The motion sensor timer is started via the start event, either track starting or self starting, with the stop event being generated by the video trigger causing the smartphone to transmit the RF stop request with the motion sensor memory saving the time value on receipt of the RF stop request.

In the case of a deaf athlete, the motion sensor 2 can be modified to set off vibration signals in place of the acoustic element as disclosed in FIG. 3 and FIG. 4.

In longer outdoor racing events, such as marathons, it may be desirable as shown in FIG. 1 to use at least one small automatic motion sensor camera 3A mounted on a tripod 4A or strapped to a pole or tree at a preselected intermediate position shown along the course of the race to accurately record and relay to the smart device a record of the time frame it takes the athlete to reach an earlier segment of the race course before the final finish line. Proper pacing of the race can be practiced in this way. Amongst trail mounted motion cameras a preferred embodiment of the motion sensor camera is the Covert Special Ops Code Black 3G 60 LED Wireless Game Camera which uses 3G functionality and an AT&T SIM card to automatically send the media data captured from the camera 3A to the athlete's smartphone 3 previously set up at the finish line of the race course.

One known prior art app called the "Sprint Stopper™" developed by Neil Quincy Alexander uses a Bluetooth speaker set up at the start line to send a series of audio beeps representing ready-set-go to time the start of the sprint and a smartphone/smart device having a camera placed on a tripod to capture the finish time of the sprint. By contrast, the present invention employs a wearable wrist motion sensor device, rather than a stationary audio speaker, to initiate the ready-set-go beeps and to sense the biometric motions of the athlete beginning the sprint start with sensing of the runner reaction time as part of the overall run time.

The principles disclosed by the present invention may also be applied by way of example to racing in other sports and competitions such as Olympic track and field running in the triathlon and pentathlon, walk running, track running, marathon running, relay running, hurdling, steeplechase running, pole vault running and broad jump running. The invention may also be applied to drill and improve the "running start" time portion of the Olympic Bobsled and Skelton sledding races.

The principles and concepts disclosed in the instant application may also be readily applied to sports and contests requiring running skills such as in soccer, rugby, American football, basketball, baseball, field hockey, lacrosse, tennis, and volleyball.

The principles and concepts disclosed in the instant invention may also be applied to other timed racing sports such as speed ice skating, relay ice skating, hockey skating, roller skating, and skate boarding.

The principles and concepts disclosed in the instant invention may also be applied wherein the race is a bicycling sports activity from at least one of a group comprising: triathlon cycling, BMX cycling, mountain bike cycling, road cycling, track cycling, and marathon cycling.

The principles and concepts disclosed in the instant invention may also be applied wherein the race is a military fitness exercise activity from at least one of a group of U.S. Army combat readiness tests (ACRT) comprising 1½ mile running in IOTV (Improved Outer Tactical Vest) and boots with obstacles to traverse, a 2 mile run, a shuffled run of 40 meters on a T course, a sprint hand carrying two 40 pound kettle weights, and a combined 250 meter shuffle, sprint, and drag of a 90 pound sled for 50 meters and crawling through an obstacle course.

The principles and concepts disclosed in the instant invention may also be applied to water sports races from one of a group comprising: swimming one or more speed laps, relay swimming, marathon swimming, triathlon swimming, water polo swimming, rowing, white water canoeing, canoe slalom, canoe sprinting, water board sailing and boat sailing.

The principles and concepts disclosed in the instant invention may be applied to snow racing sports activity from at least one of a group comprising: snowboarding, cross-country biathlon skiing, cross country skiing, Nordic combined cross-country skiing, and Alpine skiing including the Downhill, Super G, Giant Slalom, Slalom and Combined.

Modified photo stamp time apps may be used to time each lap of such events. A water proof smart device and motion sensor can be employed for a swimming event. The athlete is free to set up or modify conditions of many drills, such as the length of zigzag patterns or how many steps climbed. Many cross fit exercises may also be chosen requiring only the athlete's presence to time the event.

The athlete uses a Bluetooth® protocol to transfer the motion sensor's clock's start time to the smartphone. Other protocols, such as a Wi-Fi protocol may also be used to transfer the start time. Various modifications to the preferred embodiments and the generic terms, principles, features and advantages of the present invention expressed in the written description and figures should not be limited to the exact construction and operation as illustrated and described. Many modifications, changes and equivalents will be readily apparent to those skilled in the art, as for example, other smart devices than smartphones, such as laptops or tablets, which are readily portable and have a camera may be substituted for the smartphone and are inted to fall within the scope of the invention which is not intended to be limited to the embodiments disclosed but is to be accorded the widest scope consistent with the principles and features described.

What is claimed is:

1. A method whereby an athlete accurately self-times a premeasured distance to be run by the athlete wherein the premeasured distance has a starting line and a finish line defining the premeasured distance comprising the steps of:
   (a) prepositioning at the finish line a smartphone having a camera with a photo stamp trigger aimed at the finish line and further having a time base acting as a smartphone timer;
   (b) loading the smartphone with a photo stamp time app to record a run's finish time, T(Stop);
   (e) wearing a motion sensor having a free running clock and time base acting as a motion sensor timer;
   (d) loading the smartphone with an app to detect RF proximity of the motion sensor;
   (e) executing a one-time crystal calibration routine to characterize a relative time base drift error, T(Error), between the smartphone time base and the motion sensor time base;
   (f) selecting a run time function from a preloaded app on the smartphone to send a sync command to the motion sensor and the smartphone to zero out the timer of the smartphone and the timer of the motion sensor;
   (g) beginning at the starting line a start time, T'(Start), for the motion sensor timer;
   (h) turning off the motion sensor timer upon capturing Start Time, T'(Start) wherein T'(Start)=T(Start)+T(Error);
   (i) passing the finish line to trigger the camera to capture the finish time, T(Stop);
   (j) sending a RF signal stop timer, T(Stop), from the smartphone to the motion sensor timer to capture Start Time, T'(Start);
   (k) using the results of the crystal calibration routine to remove relative time base drift error, T(Error) based on operating system of smartphone from T'(Start) to give T(Start);
   (l) using the smartphone app to calculate the Time of the Run, T(Run) as T(Run) s T(Stop)–T'(Start)–T(Error)=T(Stop)–{T(Start)+T(Error)}–T(Error)=T(Stop)–T(Start).

2. The method of claim 1 wherein the start time, T'(Start), for the motion sensor timer, is begun by the step of the athlete selecting from one of a track start or a self start.

3. The combination of a smartphone having a time base acting as a smartphone timer and a motion sensor having a time base acting as a motion sensor timer whereby an athlete when wearing the motion sensor accurately self-times a premeasured distance to be run by the athlete wherein the premeasured distance has a starting line and a finish line defining the premeasured distance,
   the smartphone further including:
   a camera aimed at the finish line,
   a preloaded photo stamp time app triggered by the camera to record a run's finish time, T(Stop),
   a detector to detect a RF proximity of the motion sensor,
   a one-time crystal calibration routine to characterize a relative time base drift error, T(Error), between the smartphone timer base and the motion sensor time base, a preloaded app on the smartphone used to select a run time function to send a sync command to the motion sensor and the smartphone to zero out the timer of the smartphone and the timer of the motion sensor; the motion sensor further including an app for the time base of the motion sensor to capture a start time for the motion sensor timer, T'(Start), wherein T'(Start)=T(Start)+T(Error), when activated at the starting line by a track start or a self start;

the smartphone having the app to send a RF signal stop timer, T(Stop), to the motion sensor timer causing the motion sensor timer to send the start time, T' (Start), to the smartphone; the smartphone having the app which uses the results of the crystal calibration routine to remove relative time base drift error, T(Error), based on operating system of the smartphone from T'(Start) to give T(Start);

the smartphone having the app to calculate the Time of the Run, T(Run) as T(Riro)=T(Stop)−T'(Start)−T(Error)=T(Stop)−{T(Start)+T(Error)}−T(Error)=T(Stop)−T(Start).

4. The combination of a smartphone having a time base and a motion sensor having a time base wherein the smartphone includes a camera with a preloaded photo stamp time app used to trigger the camera to detect a finish time T(Stop) of a run over a predetermined distance by an athlete wearing the motion sensor, the motion sensor having a one-time crystal calibration routine based on an operating system of the smartphone to characterize a relative time drift between the time base of the smartphone and the time base of the motion sensor T(Error), the smartphone having the app for selecting a run time function and send a RF sync command signal to both the smartphone time base and the motion sensor time base to zero out their respective time bases, the motion sensor time base including a timer activated upon the start of the run to capture a starting time of the run T'(Start).

5. The combination of claim 4 wherein the smartphone includes the app to calculate a true run time start T(Start) by removing the T(Error) from the captured time T'(Start).

6. The combination of claim 5 wherein the smartphone has the app used to calculate the time of the run T(Run) by subtracting T(Start) from T(Stop).

7. The combination of claim 4 wherein the one-time crystal calibration routine results in a residual error of less than +/−8 ms in a synchronization of the time base of the smartphone and the time base of the motion sensor.

8. The combination of claim 4 wherein the RF sync command signal received by the motion sensor is factory calibrated to remove a timing error caused by a time delay in transmitting the RF sync command signal to the motion sensor by the smartphone.

9. The combination of claim 4 wherein the time base of the motion sensor timer of the motion sensor captures T'(Start) when the athlete begins either a track start or a self start at the start of the run.

10. The combination of a smartphone having a time base and a motion sensor having a time base wherein the smartphone includes a camera with a preloaded photo stamp time app used to trigger the camera to detect a finish time T(Stop) of a race over a predetermined distance by an athlete wearing the motion sensor, the motion sensor having a one-time crystal calibration routine based on an operating system of the smartphone to characterize a relative time drift between the time base of the smartphone and the time base of the motion sensor T(Error), the smartphone having the app for selecting a race time function and send a RF sync command signal to both the smartphone time base and the motion sensor time base to zero out their respective time bases, the motion sensor time base including a timer activated upon the start of the race to capture a starting time of the race T5(Start).

11. The combination of claim 10 wherein the race is running in a sports activity from at least one of a group comprising: a track run, a marathon run, a hurdles run, a walk run, a steeplechase run, a marathon run, a soccer or football run, a baseball run, a basketball run, a tennis run, a volleyball run, a field hockey run, a lacrosse run, triathlon run, a pentathlon run, a rugby run, a pole vault run and a broad jump run.

12. The combination claim 10 wherein the race is a skating sports activity from at least one of a group comprising: speed ice skating, ice hockey, roller skating and skateboarding.

13. The combination of claim 10 wherein the race is a water sports activity from at least one of a group comprising: swimming one or more speed laps, relay swimming, triathlon swimming, water polo swimming, rowing, white water canoeing, canoe slalom, canoe sprinting, water board sailing and boat sailing.

14. The combination of claim 10 wherein the race is a snow skiing sports activity from at least one of a group comprising: snowboarding, cross-country biathlon skiing, cross country skiing, Nordic combined cross-country skiing, and Alpine skiing including the Downhill, Super G, Giant Slalom, Slalom and Combined.

15. The combination of claim 10 wherein the race is a sledding sports activity from at least one of a group comprising: the Olympic Bobsled and Skeleton as it pertains to the timing of the 'running start" portion of the sledding sports activity.

16. The combination of claim 10 wherein the race is a bicycling sports activity from at least one of a group comprising: triathlon cycling, BMX cycling, mountain bike cycling, road cycling, and track cycling.

17. The combination of claim 10 wherein the race is an obstacle course race from at least one of a group comprising: mountain climbing, barrier climbing, trail hiking, water fording, and combinations thereof.

18. The combination of claim 10 wherein the race is a military fitness exercise activity from at least one of a group of U.S. Army combat readiness tests (ACRT) comprising 1½ mile running in IOTV (Improved Outer Tactical Vest) and boots with obstacles to traverse, a 2 mile run, a shuffled run of 40 meters on a T course, a sprint hand carrying two 40 pound kettle weights, and a combined 250 meter shuffle, sprint, and drag of a 90 pound sled for 50 meters.

19. The combination of claim 10 further comprising at least one automatic motion sensor camera set up at an intermediate position along the predetermined distance of the race paired with the smartphone to record and transmit to the smartphone at least one athlete's race time at the predetermined position along the race.

20. The combination of claim 10 wherein the one-time crystal calibration routine results in a residual error of less than +/−8 ms in the synchronization of the time base of the smartphone and the time base of the motion sensor.

21. The combination of claim 10 wherein the timer of the motion sensor's time base is activated by the athlete selecting one of a track start or self start.

* * * * *